United States Patent
Köhler et al.

(10) Patent No.: US 9,538,956 B2
(45) Date of Patent: Jan. 10, 2017

(54) MODIFICATION OF A TREATMENT PLAN USING MAGNETIC RESONANCE DATA ACQUIRED DURING A COOLING PERIOD

(71) Applicant: KONINKLIJKE PHILIPS N.V., Eindhoven (NL)

(72) Inventors: Max Oskar Köhler, Vantaa (FI); Erkki Tapani Vahala, Vantaa (FI); Jukka Ilmari Tanttu, Espoo (FI); Jaakko Juhani Tölö, Vantaa (FI)

(73) Assignee: Koninklijke Philips N.V., Eindhoven (NL)

( * ) Notice: Subject to any disclaimer, the term of this patent is extended or adjusted under 35 U.S.C. 154(b) by 52 days.

(21) Appl. No.: 14/382,573

(22) PCT Filed: Feb. 26, 2013

(86) PCT No.: PCT/IB2013/051537
§ 371 (c)(1),
(2) Date: Sep. 3, 2014

(87) PCT Pub. No.: WO2013/132385
PCT Pub. Date: Sep. 12, 2013

(65) Prior Publication Data
US 2015/0073261 A1 Mar. 12, 2015

Related U.S. Application Data

(60) Provisional application No. 61/606,611, filed on Mar. 5, 2012.

(30) Foreign Application Priority Data

Mar. 5, 2012 (EP) .................................... 12158033

(51) Int. Cl.
*A61B 5/00* (2006.01)
*A61N 7/02* (2006.01)
(Continued)

(52) U.S. Cl.
CPC ............... *A61B 5/4836* (2013.01); *A61B 5/01* (2013.01); *A61B 5/055* (2013.01); *A61B 18/14* (2013.01);
(Continued)

(58) Field of Classification Search
CPC ............. A61B 5/00; A61B 5/055; A61B 5/01; A61B 18/18; A61B 18/20; A61N 7/02; A61N 1/40; A61F 7/00
See application file for complete search history.

(56) References Cited

U.S. PATENT DOCUMENTS 6,065,072 A * 5/2000 Flath ............................... 710/29
6,374,132 B1 4/2002 Acker
(Continued)

FOREIGN PATENT DOCUMENTS

JP 2001231762 A 8/2001
WO 2010122449 A1 10/2010
(Continued)

OTHER PUBLICATIONS

Soher et al., Noninvasive Temperature Mapping With MRI Using Chemical Shift Water-Fat Separation, Magn Reson Med. May 2010, 63, 5, 1238-1246.*

(Continued)

*Primary Examiner* — Bo J Peng

(57) ABSTRACT

A medical apparatus (300, 400, 500, 600) comprising a magnetic resonance imaging system (302). The medical apparatus further comprises a heating system (320, 502, 601) operable for heating a target zone (321) and a processor (326). Execution of machine readable instructions causes the processor to receive (100, 200, 700, 800) a treatment plan (340). Execution of the instructions further cause the processor to repeatedly: control (102, 204, 704, 804, 900, 1002) the heating system, using the treatment plan, to heat the (Continued)

target zone during alternating heating periods and cooling periods; acquire (104, 208, 702, 706, 802, 806, 902, 906, 1000, 1004) magnetic resonance data using the magnetic resonance imaging system, and modify (110, 214, 712, 812, 1008) the treatment plan using the magnetic resonance data. The instructions cause the processor to acquire the magnetic resonance data during a cooling period selected from at least one of the cooling periods.

19 Claims, 10 Drawing Sheets

(51) Int. Cl.
| | | |
|---|---|---|
| *A61B 5/055* | (2006.01) | |
| *A61B 18/18* | (2006.01) | |
| *G01R 33/48* | (2006.01) | |
| *A61B 18/14* | (2006.01) | |
| *A61B 5/01* | (2006.01) | |
| *A61B 18/20* | (2006.01) | |
| *A61F 7/00* | (2006.01) | |
| *A61N 1/40* | (2006.01) | |
| *G01R 33/24* | (2006.01) | |
| *A61B 18/00* | (2006.01) | |

(52) U.S. Cl.
CPC .......... *A61B 18/1815* (2013.01); *A61B 18/20* (2013.01); *A61F 7/00* (2013.01); *A61N 1/403* (2013.01); *A61N 7/02* (2013.01); *G01R 33/4804* (2013.01); *G01R 33/4808* (2013.01); *A61B 5/7207* (2013.01); *A61B 34/10* (2016.02); *A61B 2018/00577* (2013.01); *A61B 2018/00642* (2013.01); *A61B 2018/00791* (2013.01); *A61B 2018/1807* (2013.01); *A61B 2090/374* (2016.02); *A61F 2007/0095* (2013.01); *G01R 33/243* (2013.01); *G01R 33/4814* (2013.01)

(56) References Cited

U.S. PATENT DOCUMENTS

| | | | |
|---|---|---|---|
| 2003/0102864 A1* | 6/2003 | Welch et al. | 324/307 |
| 2004/0039280 A1* | 2/2004 | Wu et al. | 600/412 |
| 2006/0206105 A1* | 9/2006 | Chopra | A61B 5/055 606/27 |
| 2007/0230757 A1 | 10/2007 | Trachtenberg | |
| 2007/0238976 A1* | 10/2007 | Ishihara | 600/411 |
| 2008/0275331 A1* | 11/2008 | Tseng et al. | 600/411 |
| 2009/0088623 A1 | 4/2009 | Vortman | |

FOREIGN PATENT DOCUMENTS

| | | |
|---|---|---|
| WO | 2011080631 A2 | 7/2011 |
| WO | 2011080664 A1 | 7/2011 |

OTHER PUBLICATIONS

Khokhlova et al., Magnetic resonance imaging of boiling induced by high intensity focused ultrasound, J. Acoust. Soc. Am. 125, Apr. 4, 2009.*

Rieke et al., MR Thermometry, J Magn Reson Imaging. Feb. 2008 ; 27, 2: 376-390.*

Haeusler et al., Stroke risk associated with balloon based catheter ablation for atrial fibrillation: Rationale and design of the MACPAF Study, BMC Neurology 2010, 10:63.*

* cited by examiner

MODIFICATION OF A TREATMENT PLAN USING MAGNETIC RESONANCE DATA ACQUIRED DURING A COOLING PERIOD

CROSS-REFERENCE TO PRIOR APPLICATIONS

This application is the U.S. National Phase application under 35 U.S.C. §371 of International Application No. PCT/IB2013/051537, filed on Feb. 26, 2013, which claims the benefit of U.S. Provisional Patent Application No. 61/606,611, filed on Mar. 5, 2012 and European Patent Application No. 12158033.6, filed on Mar. 5, 2012. These applications are hereby incorporated by reference herein.

TECHNICAL FIELD

The invention relates to magnetic resonance control of a heating system, in particular it relates to the modification of a treatment plan using magnetic resonance data acquired during a cooling period.

BACKGROUND OF THE INVENTION

Magnetic resonance thermometry may be used to determine either the absolute temperature of a volume or a change in temperature, depending upon the technique used. For determining the absolute temperature several magnetic resonance peaks are typically measured. Methods which measure changes in temperature are typically faster and have been used to take temperature measurements for guiding thermal treatments. For example Proton resonance frequency shift based MR thermometry may be employed to provide temperature maps in water inside the tissue during the ablation procedure for real-time feedback control of the heating process.

In high-intensity focused ultrasound (HIFU) therapy, reliable real-time temperature monitoring using e.g. Magnetic Resonance Imaging (MRI) is necessary to ensure a sufficient thermal necrosis to the target while avoiding excessive heating and damage of surrounding healthy tissues. To achieve sufficient temporal and spatial resolution, fast imaging is required preferably with a high spatial resolution while maintaining a sufficient SNR for reconstruction of reliable temperature measurements.

SUMMARY OF THE INVENTION

The invention provides for a medical apparatus, a computer program product, and a method in the independent claims. Embodiments are given in the dependent claims.

When performing temperature monitoring using magnetic resonance imaging the thermal magnetic resonance data may be acquired from a spatially limited region and/or may have a high temporal resolution in order to obtain data quickly enough to be of use for guiding the heating. A difficulty with using such data is that it may be difficult to accurately assess damage to tissue or to determine spatially dependent physical properties of the subject. Embodiments of the invention may address this or other problems by acquiring more detailed magnetic resonance data during one or more cooling periods. For instance when a tissue region is being heated by a heating system the heating may not be continuous. It may be desirable to alternate heating and cooling periods to avoid overheating sensitive regions of the subject. It may be possible to acquire more detailed or different magnetic resonance data during the cooling period, because the heating system is not actively heating a target zone and there is no longer the requirement to actively monitor the target zone to ensure that other regions of the subject are not overheated. This may enable better assessment of damage to tissue by the heating and or determination of the physical state of regions that have been heated and surrounding regions.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

'Computer memory' or 'memory' is an example of a computer-readable storage medium. Computer memory is any memory which is directly accessible to a processor. Examples of computer memory include, but are not limited to: RAM memory, registers, and register files.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'processor' as used herein encompasses an electronic component which is able to execute a program, execute a machine executable instruction, or be programmed. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computer or computing device device should also be interpreted to possibly refer to a collection or network of computing devices each comprising a processor or processors. Many programs have their instructions performed by multiple processors that may be within the same computing device or which may even be distributed across multiple computing devices.

A processor also encompasses a controller, a programable logic controller, a PID controller, a distributed control system (DCS), and intergrated circuits which are able to be programmed by burning or setting fuses.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCPIP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

Magnetic resonance data may comprise the measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonance frequency.

The proton density depends linearly on the equilibrium magnetization. It is therefore possible to determine temperature changes using proton density weighted images.

The relaxation times T1, T2, and T2-star (sometimes written as T2*) are also temperature dependent. The reconstruction of T1, T2, and T2-star weighted images can therefore be used to construct thermal or temperature maps.

The temperature also affects the Brownian motion of molecules in an aqueous solution. Therefore pulse sequences which are able to measure diffusion coefficients such as a pulsed diffusion gradient spin echo may be used to measure temperature.

One of the most useful methods of measuring temperature using magnetic resonance is by measuring the proton resonance frequency (PRF) shift of water protons. The resonance frequency of the protons is temperature dependent. As the temperature changes in a voxel the frequency shift will cause the measured phase of the water protons to change. The temperature change between two phase images can therefore be determined. This method of determining temperature has the advantage that it is relatively fast in comparison to the other methods. The PRF method is discussed in greater detail than other methods herein. However, the methods and techniques discussed herein are also applicable to the other methods of performing thermometry with magnetic resonance imaging.

Spectroscopic magnetic resonance data is defined herein as being the recorded measurements of radio frequency signals emitted by atomic spins by the antenna of a Magnetic resonance apparatus during a magnetic resonance imaging scan which contains information which is descriptive of multiple resonance peaks.

The spectroscopic magnetic resonance data may for instance be used to perform a proton spectroscopic (PS) imaging based temperature mapping method which can produce temperature maps on absolute scale. This absolute scale temperature map may therefore be used to perform a temperature calibration. This method relies on the physical principles of water proton resonance shift temperature dependence as the proton resonance frequency method, but the acquisition method is different: the frequency shift is calculated from the magnetic resonance spectra. The shift is calculated from the position difference of the water and a reference proton peak. Protons in lipids may for example be used as reference, as their resonance frequency is known to be almost independent of temperature, while the water proton peak has linear dependence on temperature. This can be done in the voxels, where both tissue types are present. If water and lipids do not exist in the same voxel, one may try to use some other tissue type than lipids as reference. If not successful, there may be some voxels where the reference peaks, and therefore the temperature data, are not available. Interpolation and/or temperature filtering may be used to help these situations, since body temperature is normally not expected to change rapidly spatially with the highly localized temperature rise typically caused by thermal therapy being an obvious exception. The utilization of reference peaks makes the method relatively independent of field drifts or inter-scan motion. Because the scanning takes a time of at least on the order of one minute with current methods, the PS method is susceptible to intra-scan motion or temperature change during scanning. In a case where temperature is constant or temperature variation is small both in time and space, the method is able to produce useful information. For example, with the Magnetic Resonance Guided High Intensity Focused Ultrasound (MR-HIFU), the PS method can be used to provide the actual body temperature distribution before start of MR-HIFU or other temperature treatment as opposed to using a spatially homogeneous starting temperature taken as the body core temperature measured with a thermometer probe. Alternatively, the PS method can be used as a sanity check for cumulated temperature between treatment heatings outside treatment area.

An 'ultrasound window' as used herein encompasses a window which is able to transmit ultrasonic waves or energy. Typically a thin film or membrane is used as an ultrasound window. The ultrasound window may for example be made of a thin membrane of BoPET (Biaxially-oriented polyethylene terephthalate).

In one aspect the invention provides for a medical apparatus comprising a magnetic resonance imaging system. The magnetic resonance imaging system comprises a magnet with an imaging zone for acquiring magnetic resonance data from a subject within the imaging zone. The imaging zone as used herein encompasses a region with a high enough magnetic field and high enough magnetic field uniformity such that it is possible to acquire magnetic resonance data from within the zone. The medical apparatus further comprises a heating system operable for heating a target zone within the imaging zone. A heating system as used herein encompasses a system or apparatus which is able to heat a local region within a subject or object. The medical apparatus further comprises a memory for storing machine executable instructions. The medical apparatus further comprises a processor for controlling the medical apparatus. Execution of the instructions causes the processor to receive a treatment plan. A treatment plan as used herein encompasses a set of instructions or data which may be used for generating a set of instructions for operating the heating system. In some embodiments the treatment plan may contain anatomical or other data descriptive of the subject.

Execution of the instructions further causes the processor to repeatedly control the heating system in accordance with the treatment plan. This is done to heat the target zone during alternating heating periods and cooling periods. The heating system is operable for heating the target zone by using the alternating heating periods and cooling periods. Execution of the instructions further cause the processor to repeatedly acquire magnetic resonance data by controlling the magnetic resonance imaging system in accordance with the first pulse sequence. A pulse sequence as herein encompasses a set of commands or a timing diagram useful for generating a set of commands. The set of commands are used to control the time dependent functioning of the magnetic resonance imaging system for acquiring the magnetic resonance data.

Execution of the instructions further causes the processor to repeatedly modify the treatment plan in accordance with the magnetic resonance data. The instructions further cause the processor to acquire the magnetic resonance data during a cooling period selected from at least one of the cooling periods.

This embodiment may be advantageous because the heating of the target zone is done using alternating heating periods and cooling periods. During the cooling period it may not be necessary to monitor the heating system in order to control the heating system. Detailed magnetic resonance data may therefore be acquired from the subject and used to refine or modify the treatment plan. If the data were acquired during the heating period the magnetic resonance data may be useful for controlling the heating system directly but may not be detailed enough to provide data which may be used to modify the treatment plan.

In one embodiment the cooling period is selected on the fly. That is to say it is not necessarily known when the heating and cooling periods will be before the procedure starts. As the heating and cooling is performed by the heating system one or more of the cooling periods can be selected for acquiring the magnetic resonance data.

In another embodiment execution of the instructions further cause the processor to repeatedly acquire control magnetic resonance data by controlling the magnetic resonance imaging system in accordance with a second pulse sequence. The control magnetic resonance data as used herein encompasses magnetic resonance data. The control magnetic resonance data is used by the processor to form a control loop for controlling the operation of the heating system. The instructions cause the processor to acquire the control magnetic resonance data during a heating period chosen from at least one of the heating periods. The heating period may be selected on the fly. The heating system is controlled in accordance with the treatment plan and the control magnetic resonance data. Essentially the treatment plan is used in conjunction with the control magnetic resonance data to form a closed control loop for controlling the operation of the heating system. This may be beneficial because there may be sensitive structures in the subject surrounding or near the target zone. Acquiring the control magnetic resonance data during the heating of the target zone may reduce the risks of accidental damage or injury.

In another embodiment the control magnetic resonance data comprises first thermal magnetic resonance data.

In another embodiment the control magnetic resonance data comprises first thermal magnetic resonance data. The magnetic resonance data comprises second thermal magnetic resonance data. Execution of the instructions further causes the processor to calibrate the first thermal magnetic resonance data using the second thermal magnetic resonance data. For instance the first thermal magnetic resonance data may be frequency shift data and the second thermal magnetic resonance data may, for instance, be nuclear magnetic resonance spectral data which enables the calculation of absolute or true temperatures.

In another embodiment the control magnetic resonance data comprises first thermal magnetic resonance data. The magnetic resonance data comprises second magnetic resonance thermometry data. The first thermal magnetic resonance data has a first temporal resolution. The second thermal magnetic resonance data has a second temporal resolution. The first temporal resolution is higher than the second temporal resolution. This embodiment may be beneficial because if the magnetic resonance data has a lower temporal resolution the measurement of the temperature may be more accurate. In this respect the first temporal resolution is for when the zone is being actively heated. During active heating it is important to receive data which is real time or acquire it in very short intervals to help avoid the chance of injury or damage of the subject. However, when the system is in a cooling mode it is safe to use a lower temporal resolution so that the timeliness of the data is not so critical. The data acquired at the second temporal resolution may be used to make more accurate measurements and used to modify the treatment plan.

In another embodiment the thermometry sequence is changed in order to provide more reliable temperature estimates with a lower temporal resolution that were used during the sonication or heating.

In another embodiment the thermometry sequence is changed or pulse sequence is changed in order to provide more reliable temperature estimates with the lowest temporal resolution than was used during sonication or heating. The lower temporal resolution may result in a higher signal-to-noise ratio which gives a more reliable temperature.

In another embodiment execution of the instructions further causes the processor to control the magnetic resonance imaging system such that the control magnetic resonance data is acquired from a first region of interest. Execution of the instructions further causes the processor to control the magnetic resonance imaging system such that the magnetic resonance data is acquired from a second region of interest. In one embodiment the first region of interest is smaller than the second region of interest. In an alternative embodiment the first region of interest and the second region of interest have an identical area. The second region of interest is shifted with respect to the first region of interest. This means that they may be in a different physical location. In an alternative embodiment the first region of interest has a first area. The second region of interest has a second area. The second area is greater than the first area.

In another embodiment the first pulse sequence is operable for controlling the magnetic resonance imaging system such that the magnetic resonance data has less geometric distortion than the control magnetic resonance data. This may be beneficial because if there is less geometric distortion then the images provided by the magnetic resonance data may be more accurate or have fewer artifacts.

In another embodiment the first pulse sequence is gradient echo or multi echo gradient echo pulse sequence. The second pulse sequence is an gradient echo EPI pulse sequence. In another embodiment larger or different anatomical coverage is taken between the control and regular magnetic resonance data.

In another embodiment the heating system comprises a high intensity focused ultrasound system with a moveable transducer. Execution of the instructions further cause the processor to move the transducer between a first position and a second position after the magnetic resonance data has been acquired once so essentially the magnetic resonance data may be acquired when the transducer is at the first position and then later when it's in the second position. Execution of the instructions further cause the processor to calculate a phase map using the magnetic resonance data. The physical change in the location of the transducer may cause a change in the phase map.

In another embodiment the phase map is calculated using the magnetic resonance data acquired from the first and second positions.

In another embodiment execution of the instructions further cause the processor to calculate a corrected temperature map using the thermal magnetic resonance data and the phase map.

In another embodiment the first pulse sequence comprises a fat temperature measuring pulse sequence. The magnetic resonance data is acquired at least two times. Execution of the instructions further causes the processor to calculate a near field fat temperature map using the magnetic resonance data. The near field as used herein encompasses a region of the subject between the target zone and the heating system.

In another embodiment the baseline temperature used in the proton resonance frequency temperature map may be calibrated with alternative temperature sequences using a different resolution or temperature imaging technique. This may be beneficial because the proton resonance frequency method is a relative technique and is beneficial to calibrate it.

In another embodiment the pulse sequence is for measuring a fat temperature such as a so called spectral method.

In another embodiment each parameter of the treatment plan can be automatically or user controlled.

In another embodiment the treatment plan can be automatically changed or modified by the doctor.

In another embodiment changes to the heating or sonication can be the sonication or heating order, cooling times can be changed, heating times can be changed, cell size can be changed, the target size can be changed and the heating and cooling duration may also be modified. A cell as used herein encompasses a volume that is heated.

In another embodiment the magnetic resonance data is acquired at least two times. Execution of the instructions further cause the processor to reconstruct a first image and a second image from the magnetic resonance data acquired at the at least two times. Essentially the first image is acquired during a first time period and the second image is acquired during a second time period. Execution of the instructions further cause the processor to determine a motion map using the first image and the second image. Execution of the instructions further cause the processor to modify the treatment plan in accordance with the motion map. This may be beneficial because detailed images may be able to be acquired during the cooling period and this may enable accurate modification of the treatment plan to account for motion of the subject.

In another embodiment execution of the instructions further cause the processor to generate an estimated tissue damage map using the magnetic resonance imaging system by analyzing the magnetic resonance imaging data using any one of the following analysis methods: T2W imaging, constructing an elastographic map, calculating a diffusion map, determining a diffusion image, determining a non-contrast magnetic resonance angiogram, determining a perfusion map, determining an intravoxel incoherent motion map, calculating a T1 map, calculating a T1 rho map, calculating a T2-star map, calculating a nuclear magnetic resonance spectrum, and calculating oxygenation level by calculating an oxygen nuclear magnetic resonance spectrum. The treatment plan is modified in accordance with the tissue damage map.

In another embodiment the magnetic resonance data comprises magnetic resonance angiography data wherein execution of the instructions further cause the processor to determine a vessel occlusion map using the magnetic resonance angiography data. The treatment plan is modified in accordance with the tissue damage map.

In another embodiment non-contrast MRI may be used to assess vessel occlusion and allow for iteratively attempting tumor feeding vessel ablation.

In another embodiment the vessel occlusion map is also displayed on a display for a physician to interpret.

In another embodiment the heating system is a high-intensity focused ultrasound system.

In another embodiment the heating system is a radio-frequency heating system.

In another embodiment the heating system is a microwave ablation system.

In another embodiment the heating system is a hyperthermia therapy system.

In another embodiment the heating system is a laser ablation system.

In another embodiment the heating system is an infrared ablation system.

In another aspect the invention provides for a computer program product comprising machine executable instructions for execution by a processor controlling a medical apparatus. The medical apparatus comprises a magnetic resonance imaging system comprising a magnet with an imaging zone for acquiring magnetic resonance data from a subject from within the imaging zone. The medical apparatus further comprises a heating system operable for heating a target zone within the imaging zone. Execution of the machine executable instructions causes the processor to receive a treatment plan. Execution of the machine executable instructions further causes the processor to repeatedly control the heating system in accordance with the treatment plan to heat the target zone during alternating heating periods and cooling periods. Execution of the machine executable instructions further causes the processor to repeatedly acquire magnetic resonance data by controlling the magnetic resonance imaging system in accordance with the first pulse sequence. The instructions cause the processor to acquire the magnetic resonance data during a cooling period selected from at least one of the cooling periods. Execution of the machine executable instructions further cause the processor to repeatedly modify the treatment plan in accordance with the magnetic resonance data.

In another aspect the invention provides for a method of controlling a medical apparatus. The medical apparatus comprises a magnetic resonance imaging system comprising a magnet with an imaging zone for acquiring magnetic resonance data from a subject from within the imaging zone. The medical apparatus further comprises a heating system operable for heating a target zone within the imaging zone. The method further comprises the step of receiving a treatment plan. The method further comprises repeatedly performing the step of controlling the heating system in accordance with the treatment plan to heat the target zone during alternating heating periods and cooling periods. The method further comprises repeatedly acquiring magnetic resonance data by controlling the magnetic resonance imaging system in accordance with the first pulse sequence. The magnetic resonance data is acquired during a cooling period selected from at least one of the cooling periods. The method further comprises repeatedly modifying the treatment plan in accordance with the magnetic resonance data.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
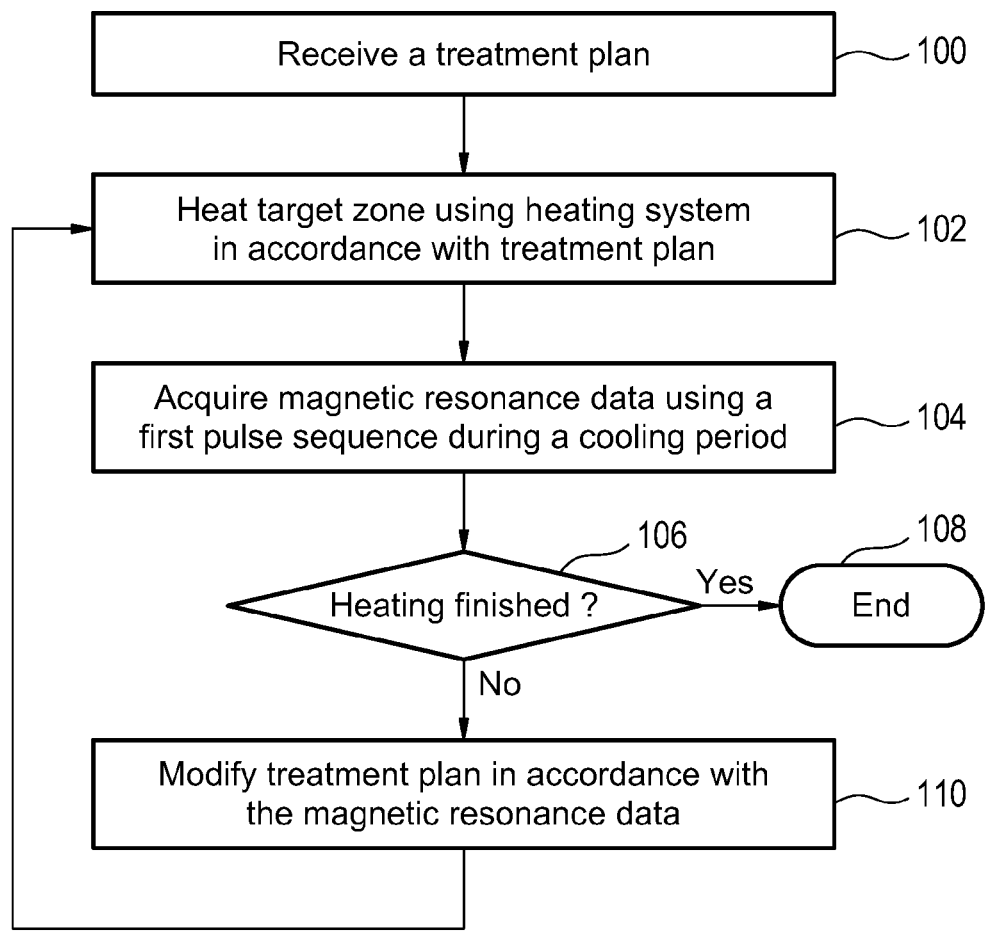
FIG. 1 shows a flowchart which illustrates a method according to an embodiment of the invention.

FIG. 1 shows a flow diagram which illustrates a method according to an embodiment of the invention. First in step 100 a treatment plan is received. Next in step 102 the target zone is heating using the heating system in accordance with the treatment plan. The treatment plan may comprise instructions which are used for directly controlling the heating system or the treatment plan may contain information which is used to generate such commands for controlling the heating system. Next in step 104 magnetic resonance data is acquired using a first pulse sequence during a cooling period. A cooling period as used herein is a period of time when the heating system is not actively heating the target zone. Next in step 106 is a decision box. The question is the heating finished. If the heating is finished then the method ends in step 108. If not then the method proceeds to step 110. In step 110 the treatment plan is modified in accordance with the magnetic resonance data. The method then proceeds back to step 102 and the target zone is again heated using the heating system. This loop from steps 102, 104, and 110 are repeated until the method ends in step 108.

Figure 2:
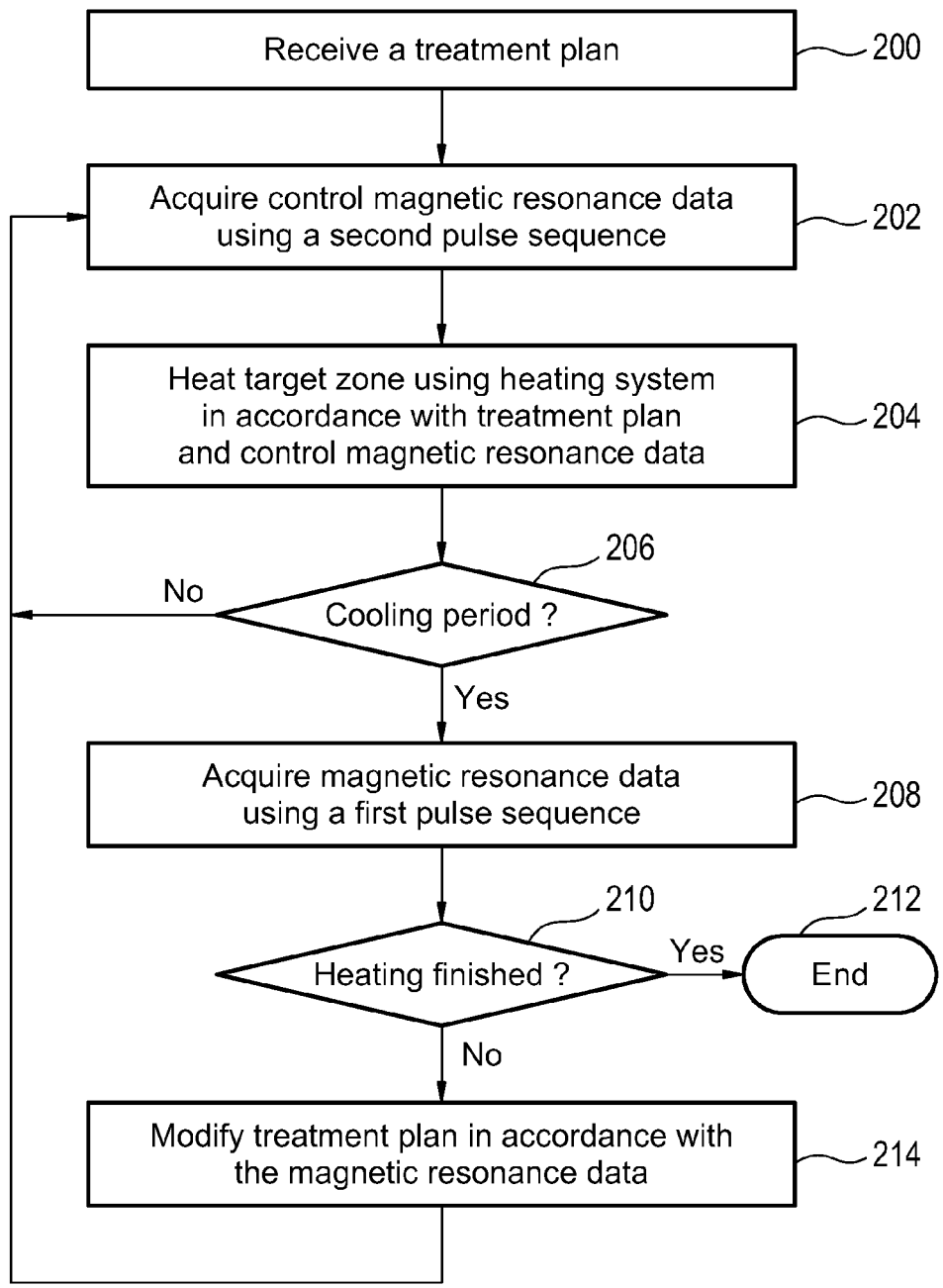
FIG. 2 shows a flowchart which illustrates a method according to a further embodiment of the invention.

FIG. 2 shows a flow diagram which illustrates a method according to a further embodiment of the invention. First in step 200 a treatment plan is received. Next in step 202 control magnetic resonance data is acquired using a second pulse sequence. Next in step 204 the target zone is heated using the heating system in accordance with the treatment plan and the control magnetic resonance data. The acquisition of the control magnetic resonance data may be performed during all or part of the period when the heating system is heating the target zone. Step 206 is a decision box and the question is the current time a cooling period. A cooling period is when the heating system is not actively heating the target zone. If this is not a cooling period then the method returns back to step 202 to perform steps 202 and 204. Steps 202 and 204 may be performed simultaneously. Essentially steps 202 and 204 form a closed control loop for control of the heating system using the magnetic resonance imaging system.

Back at step 206 if it is a cooling period then step 208 is performed. In step 208 magnetic resonance data is acquired using a first pulse sequence. In some embodiments the control magnetic resonance data may also be acquired during at least a portion of a cooling period. In some, embodiments, the control magnetic resonance data is acquired during a portion of the cooling period and then the magnetic resonance data is acquired after the acquisition of the control magnetic resonance data is finished.

Next step 210 is another decision box, is the heating finished. If the heating is finished then the method ends in step 212. If the heating is not finished then step 214 is performed. In step 214 the treatment plan is modified in accordance with the magnetic resonance data. Then the method proceeds back to step 202 and the process is repeated. In this embodiment a magnetic resonance data acquired with a second pulse sequence is used to control the heating system. During periods when the heating system is paused and not heating other magnetic resonance data is acquired using a first pulse sequence. This magnetic resonance data may be more detailed and contain different information that then was acquired using the second pulse sequence. The magnetic resonance data acquired during the cooling period is then used to modify the treatment plan.

Figure 3:
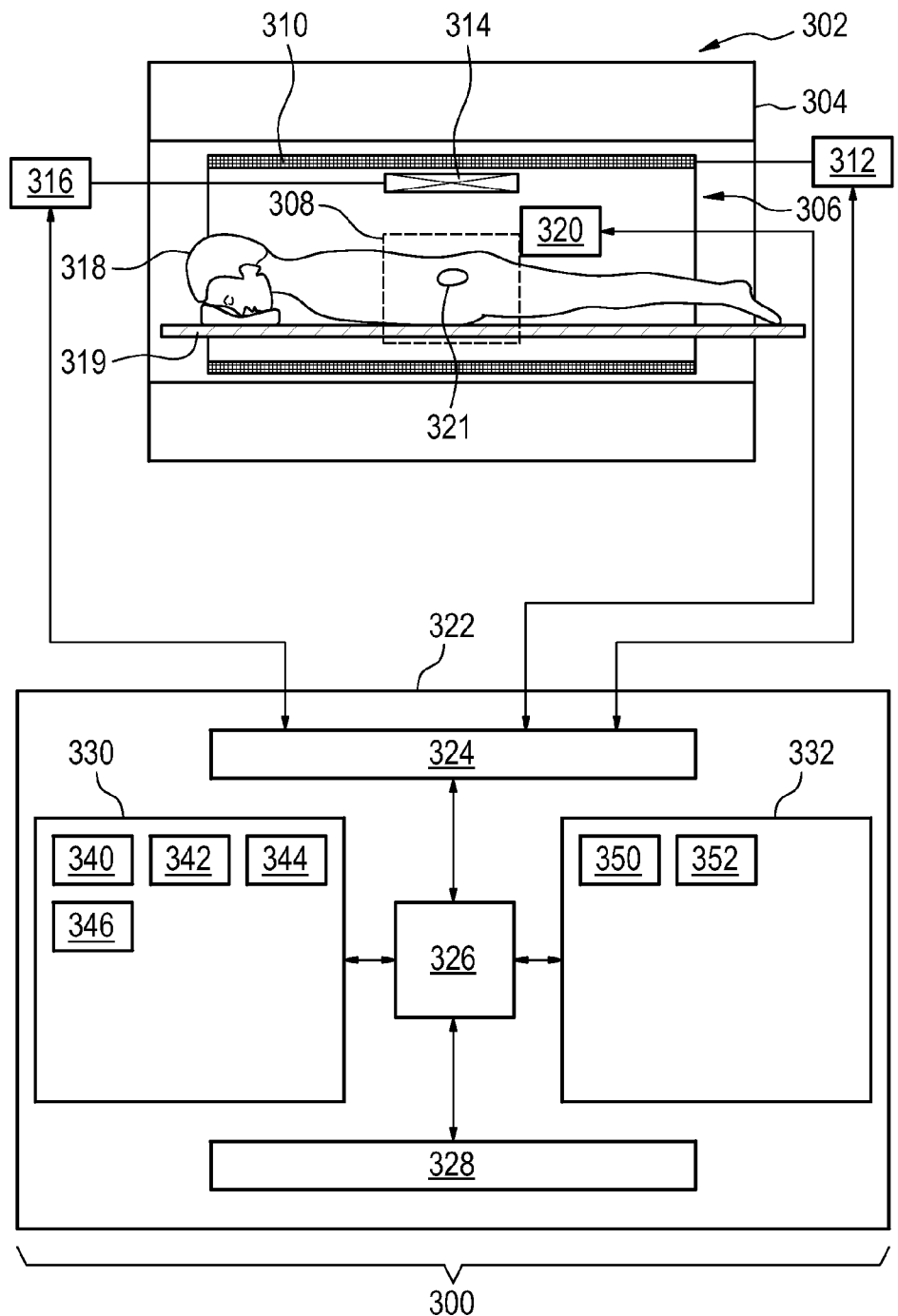
FIG. 3 illustrates a medical apparatus according to an embodiment of the invention.

FIG. 3 illustrates a medical apparatus 300 according to an embodiment of the invention. The medical apparatus 300 comprises a magnetic resonance imaging system 302. The magnetic resonance imaging system 302 is shown as comprising a magnet 304. The magnet 304 is a cylindrical type superconducting magnet with a bore 306 through the center of it. The magnet 304 has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore of the cylindrical magnet there is an imaging zone 308 where the magnetic field is strong and uniform enough to perform magnetic resonance imaging.

Also within the bore of the magnet is a magnetic field gradient coil 310 which is used for acquisition of magnetic resonance data to spatially encode magnetic spins within an imaging zone of the magnet. The magnetic field gradient coil 310 is connected to a magnetic field gradient coil power supply 312. The magnetic field gradient coil is representative. Typically magnetic field gradient coils contain three separate sets of coils for spatially encoding in three orthogonal spatial directions. A magnetic field gradient power supply 312 supplies current to the magnetic field gradient coils. The current supplied to the magnetic field coils is controlled as a function of time and may be ramped and/or pulsed.

Adjacent the imaging zone 308 is a radio-frequency coil 314. The radio-frequency coil 314 is connected to a radio-frequency transceiver 316. Also within the bore of the magnet 304 is a subject 318 that is reposing on a subject support 319 and is partially within the imaging zone 308.

Adjacent to the imaging zone 308 is a radio-frequency coil 314 for manipulating the orientations of magnetic spins within the imaging zone 308 and for receiving radio transmissions from spins also within the imaging zone 308. The radio-frequency coil 314 may contain multiple coil elements. The radio-frequency coil 314 may also be referred to as a channel or an antenna. The radio-frequency coil is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio-frequency transceiver 316 are representative. The radio-frequency coil 314 is intended to also represent a dedicated transmit antenna and a dedicated receive antenna. Likewise the transceiver 316 may also represent a separate transmitter and a separate receiver.

The medical apparatus further comprise a heating system 320. The heating system 320 is intended to be generic and may represent any system used for heating a portion of a subject. The heating system 320 may for instance be a high-intensity focused ultrasound system, a radio-frequency heating system, a microwave ablation system, a hyperthermia therapy system, a laser ablation system, and an infrared ablation system. A portion of the subject 318 is indicated as a target zone 321. The heating system 320 is able to controllably heat the target zone 321.

The magnetic field gradient coil power supply 312, the radio-frequency transceiver 316, and the heating system 320 are connected to a hardware interface 324 of a computer system 322. The computer system 322 further comprises a processor 326. The processor 326 is connected to the hardware interface 324. The hardware interface 324 enables the processor 326 to send and receive data and commands to the magnetic resonance imaging system 302. The computer system 322 further comprises a user interface 328, computer storage 330 and computer memory 332.

The computer storage is shown as containing a treatment plan 340. The computer storage 330 is further shown as containing a first pulse sequence 342. The computer storage 330 is further shown as containing magnetic resonance data 344 that was acquired using the magnetic resonance imaging system 300 with controls generated or provided by the first pulse sequence 342. The computer storage 330 is further shown as containing heating system commands 346. The heating system commands 346 may be taken from the treatment plan 340 and/or may also be modified heating system commands 346 that were modified using the magnetic resonance data 344.

The computer memory 332 is shown as containing a control module 350. The control module contains computer executable code which contains commands which enable the processor 326 to control the operation and function of the medical apparatus 300. The computer memory 332 is further shown as containing a treatment plan modification module 352. The treatment plan modification module 352 contains computer executable code which enables the processor 326 to modify the treatment plan 340 in accordance with the magnetic resonance data 344. In some instances this may include modifying the heating system commands 346. However, in this embodiment the treatment plan modification module 352 modifies the treatment plan 340 and/or the heating system commands 346 when the heating system 320 is not actively heating the target zone 321. In some embodiments the treatment plan modification module 352 may contain computer executable code for processing the magnetic resonance data 344 such that intermediary images and/or thermal maps are generated and then used for modifying the treatment plan 340.

Figure 4:
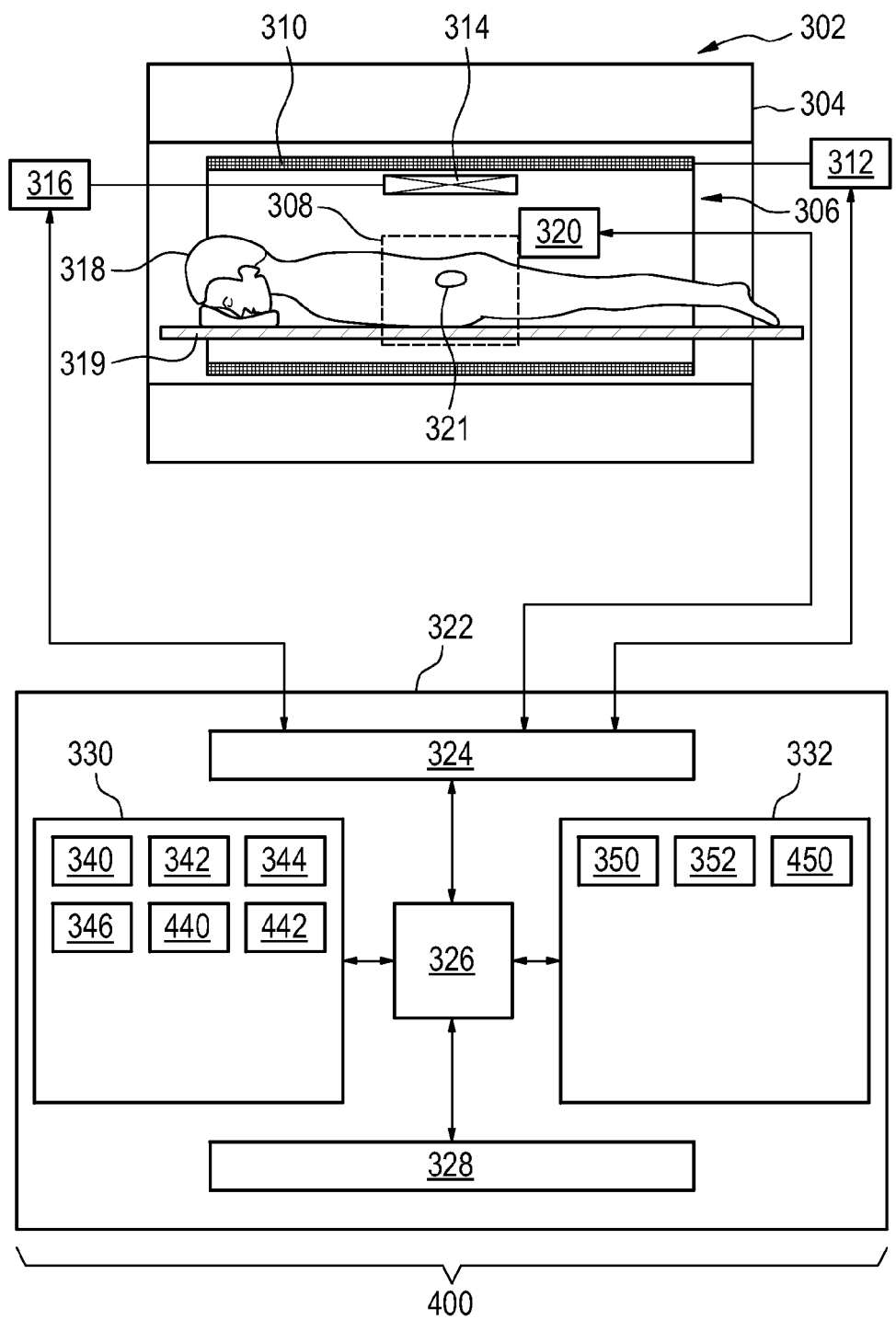
FIG. 4 illustrates a medical apparatus according to a further embodiment of the invention.

FIG. 4 illustrates a medical apparatus 400 according to a further embodiment of the invention. The embodiment shown in FIG. 4 is similar to that shown in FIG. 3. In this embodiment the computer memory 330 is shown as further containing a second pulse sequence 440. The computer memory 330 is shown as further containing control magnetic resonance data that was acquired using the magnetic resonance imaging system 302 while controlled by the second pulse sequence 440.

The computer memory 332 is shown as further containing heating system command modification module 450. The heating system command modification module 450 contains computer executable code which enables the processor 326 to modify the heating system commands 346 using the control magnetic resonance data 442. In this embodiment the heating system command modification module 450 is operable for modifying the heating system commands 346 while the control magnetic resonance data 442 is being acquired. Essentially the heating system command modification module 450 enables the processor 326 to form a closed control loop for the control of the heating system 320.

Figure 5:
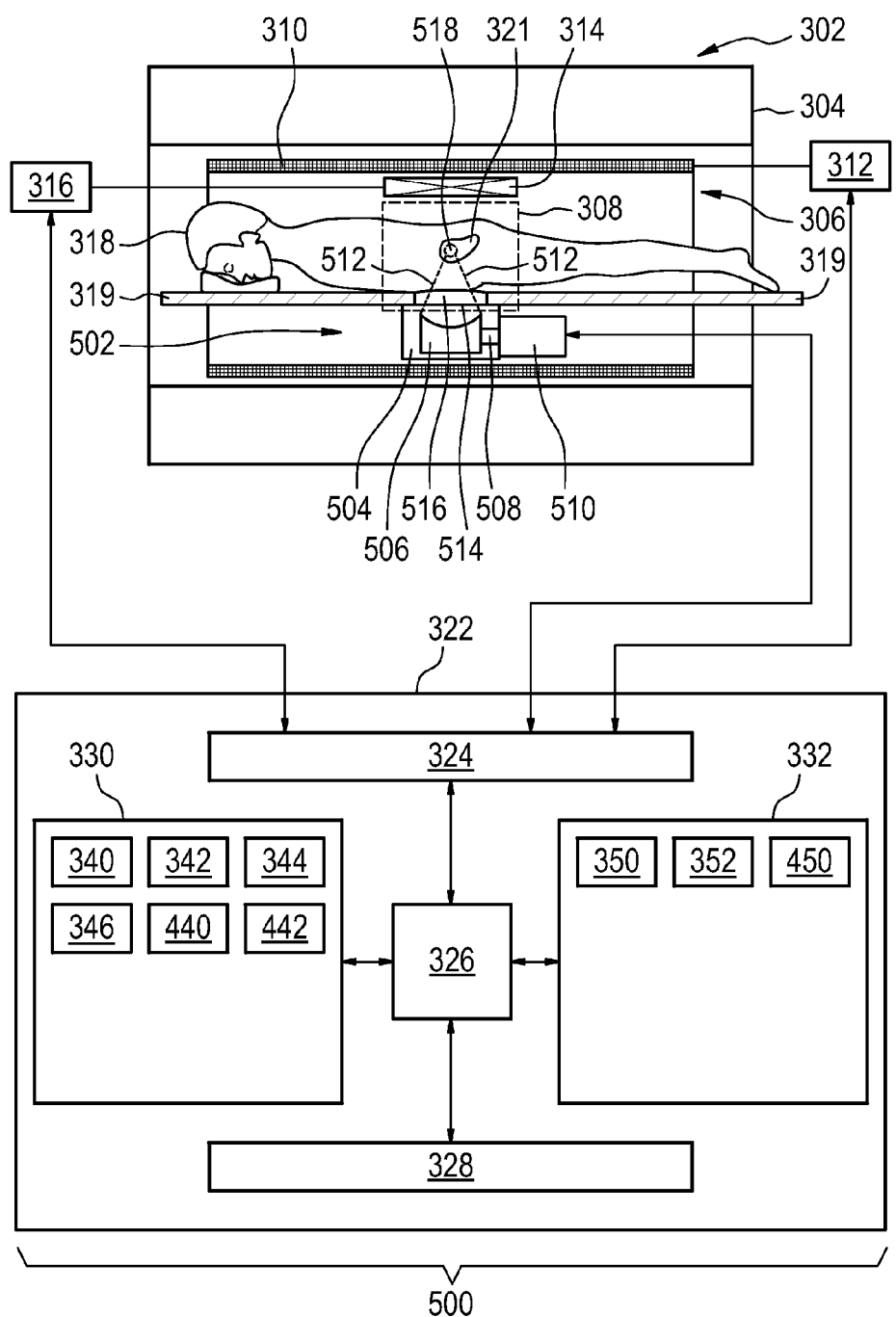
FIG. 5 illustrates a medical apparatus according to a further embodiment of the invention.

FIG. 5 shows a further embodiment of the medical apparatus 500 according to the invention. In this embodiment the heating system is a high-intensity focused ultrasound system 502. The high-intensity focused ultrasound system comprises a fluid-filled chamber 504. Within the fluid-filled chamber 504 is an ultrasound transducer 506. Although it is not shown in this Fig. the ultrasound transducer 506 may comprise multiple ultrasound transducer elements each capable of generating an individual beam of ultrasound. This may be used to steer the location of a sonication point 518 electronically by controlling the phase and/or amplitude of alternating electrical current supplied to each of the ultrasound transducer elements. The sonication point 518 is operable to be controlled to sonicate the target zone 321. In some embodiments the sonication point can be electronically moved during the sonication to create a heating cell of a predefined size.

The ultrasound transducer 506 is connected to a mechanism 508 which allows the ultrasound transducer 506 to be repositioned mechanically. The mechanism 508 is connected to a mechanical actuator 510 which is adapted for actuating the mechanism 508. The mechanical actuator 510 also represents a power supply for supplying electrical power to the ultrasound transducer 506. In some embodiments the power supply may control the phase and/or amplitude of electrical power to individual ultrasound transducer elements. In some embodiments the mechanical actuator/power supply 510 is located outside of the bore 306 of the magnet 304.

The ultrasound transducer 506 generates ultrasound which is shown as following the path 512. The ultrasound 512 goes through the fluid-filled chamber 504 and through an ultrasound window 514. In this embodiment the ultrasound then passes through a gel pad 516. The gel pad is not necessarily present in all embodiments but in this embodiment there is a recess in the subject support 319 for receiving a gel pad 516. The gel pad 516 helps couple ultrasonic power between the transducer 506 and the subject 518. After passing through the gel pad 516 the ultrasound 512 passes through the subject 518 and is focused to a sonication point 518. The sonication point 518 is being focused within a target zone 321. The sonication point 518 may be moved through a combination of mechanically positioning the ultrasonic transducer 506 and electronically steering the position of the sonication point 518 to treat the entire target zone 321.

The high-intensity focused ultrasound system 502 is shown as being also connected to the hardware interference 324 of the computer system 322. The computer system 322 and the contents of its storage 330 and memory 332 are equivalent to that as shown in FIG. 4.

Figure 6:
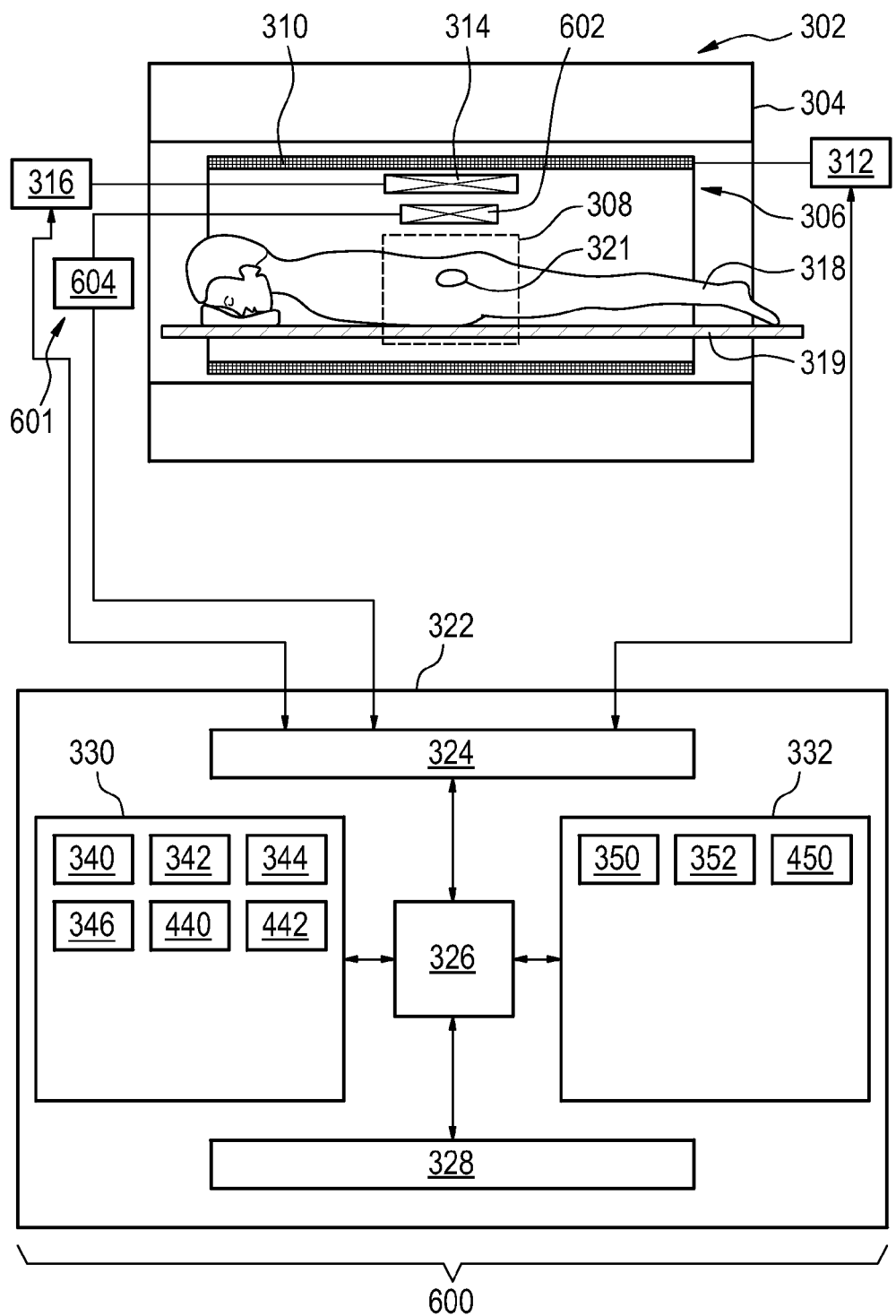
FIG. 6 illustrates a medical apparatus according to a further embodiment of the invention.

FIG. 6 illustrates a medical apparatus 600 according to a further embodiment of the invention. In this embodiment the heating system is a radio-frequency heating system 601. The embodiment shown in FIG. 6 is similar to that shown in FIG. 4. The computer system 322 of FIG. 6 is equivalent to the computer system 322 shown in FIG. 4. The contents of the computer storage 330 and the computer memory 332 are also equivalent to the computer storage 330 and the computer memory 332 as shown in FIG. 4. In the embodiment shown in FIG. 6 a radio-frequency heating system 601 is used as the heating system. The radio-frequency heating system 601 comprises an antenna 602 and a radio-frequency transmitter 604. The antenna 602 is in the vicinity of target zone 321. Radio-frequency energy generated by the transmitter 604 and radiated by the antenna 602 is used to selectively heat the target zone 321. In this embodiment the radio-frequency transmitter 604 is shown as being connected to the hardware interface 324. The processor 326 and the contents of the computer storage 330 and the computer memory 332 are used to control the radio-frequency transmitter 604 in a manner equivalent to the way the high-intensity focused ultrasound system 502 of FIG. 5 is controlled by the processor 326.

Figure 7:
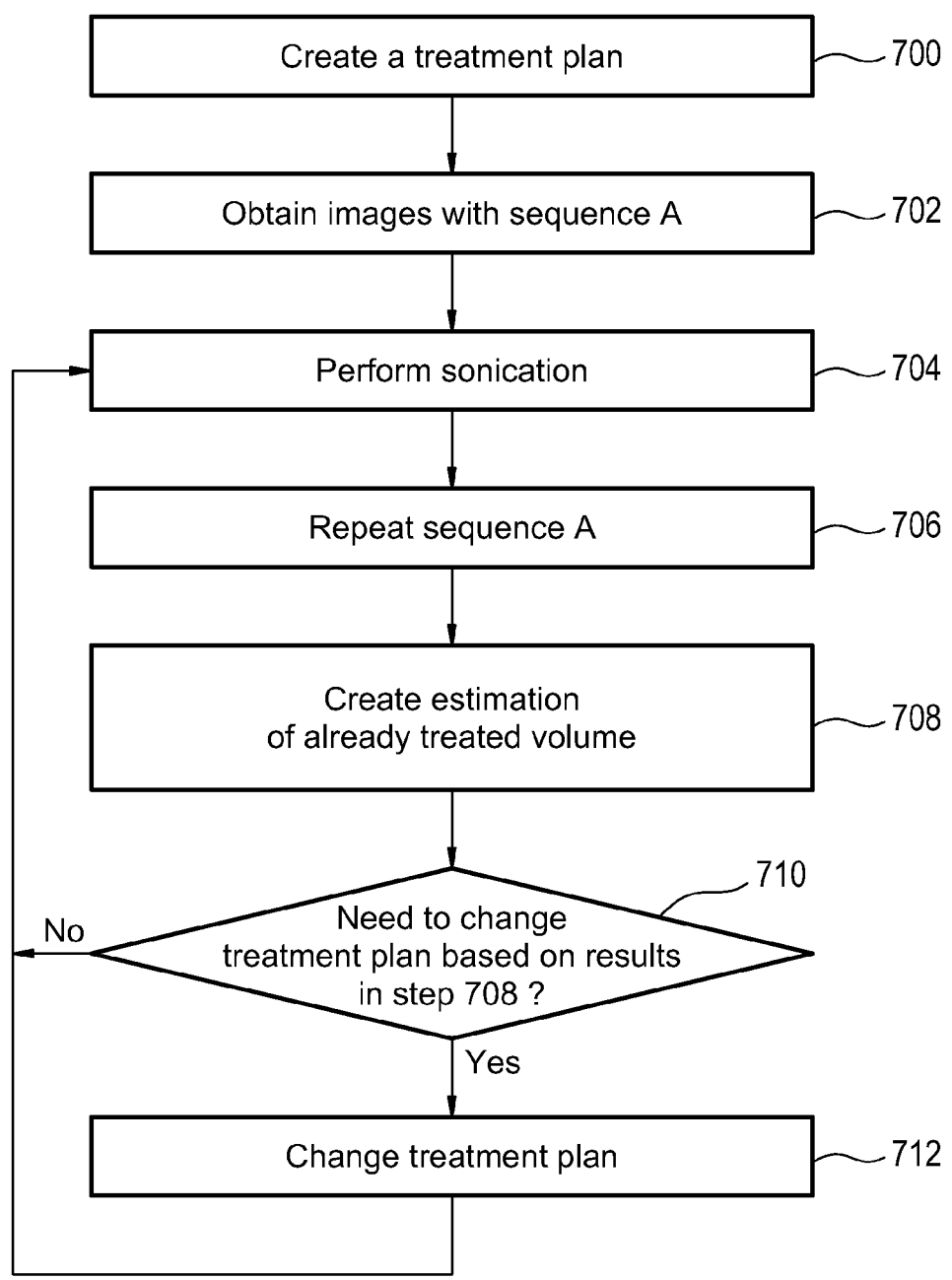
FIG. 7 shows a flowchart which illustrates a method according to a further embodiment of the invention.

FIG. 7 shows a flow diagram of a method according to a further embodiment of the invention. First in step 700 a treatment plan is received or created. Next in step 702 magnetic resonance data is acquired with a pulse sequence of type A. In this embodiment a pulse sequence of type A is operable for detecting early effect of sonification in the target tissue. For instance it may be used for detecting perfusion or diffusion or changes in the relaxation time such as the T1 and T2 relaxation time. Next in step 704 a heating of the target zone by the heating system is performed. This may include also monitoring the temperature with the magnetic resonance imaging system during the heating and possibly some time after the heating. In some embodiments the heating is performed by a sonication. Next in step 706 the pulse sequence of type A is repeated and the magnetic resonance data is re-acquired. Next in step 708 an estimate of the already treated volume is created. This may be a map of the tissue that is likely to become ablated.

Next in step 710 is a decision box. This decision is a question if it is needed to change the treatment plan based on the results in step 708. If no modification is needed then the method returns back to step 704 and the heating is re-performed. If the treatment plan needs to be modified then the method proceeds to step 712 where the treatment plan is changed in accordance with the acquired magnetic resonance data. In this method the start of each step can be performed automatically or it may be controlled by a user or operator. In some embodiments an operator may stop the method at any point. In step 710 the decision may be performed by either an operator or by an algorithm. In step 712 changes to the treatment plan may include repeating some sonication points or heating points, increasing or decreasing the overlap in heating or sonication points, also deciding that less heating or sonication is required.

Figure 8:
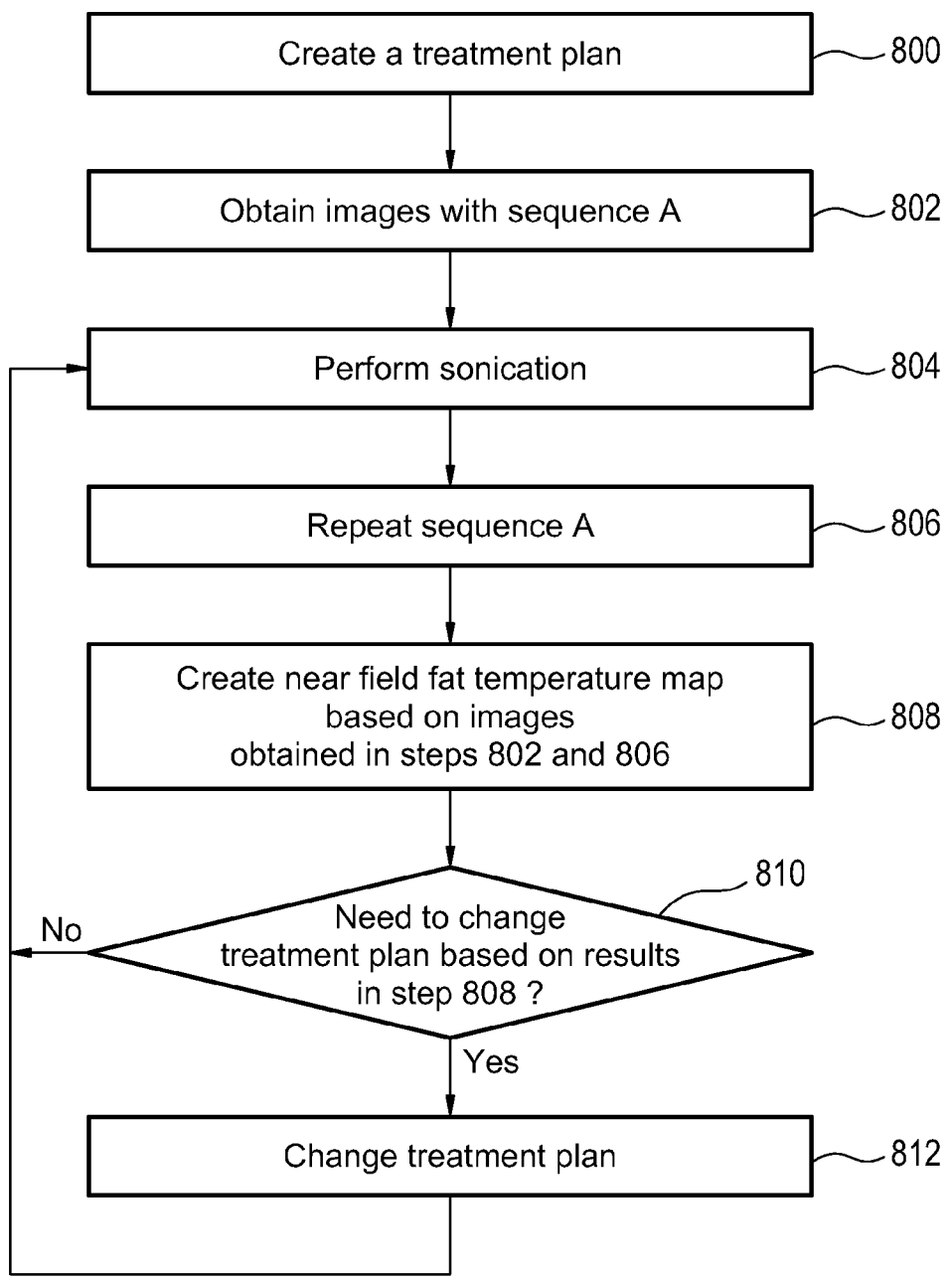
FIG. 8 shows a flowchart which illustrates a method according to a further embodiment of the invention.

FIG. 8 shows a flow diagram according to a further embodiment of the invention. In step 800 a treatment plan is received or created. Next in step 802 magnetic resonance data and/or images are acquired using a pulse sequence of type A. In this embodiment the pulse sequence of type A is a pulse sequence which is used to measure fat temperature. For instance the pulse sequence may be a pulse sequence which acquires T2 or T1 information. Next in step 804 the target zone is heated by the heating system. During the heating 804 temperature monitoring of the target zone and/or the area surrounding the target zone may be performed and possibly some time after the heating is finished. Next in step 806 the magnetic resonance data is acquired again using pulse sequence A. Next in step 808 a near field temperature map based on the images attained in step 802 and 806 is created or calculated. Next step 810 is a decision box. The decision is there a need to change the treatment plan based on the results in step 808. In this case the change may be using longer cooling periods or to change cell positions to avoid excessive cumulative heating resulting tissue damage in near field region. Typically near field region contains subcutaneous fat, If the answer is no then the method returns back to step 804 where the target zone is heated. If yes then step 812 is performed. In step 812 the treatment plan is modified using the magnetic resonance data that was acquired and then the method returns back to the heating step 804.

Figure 9:
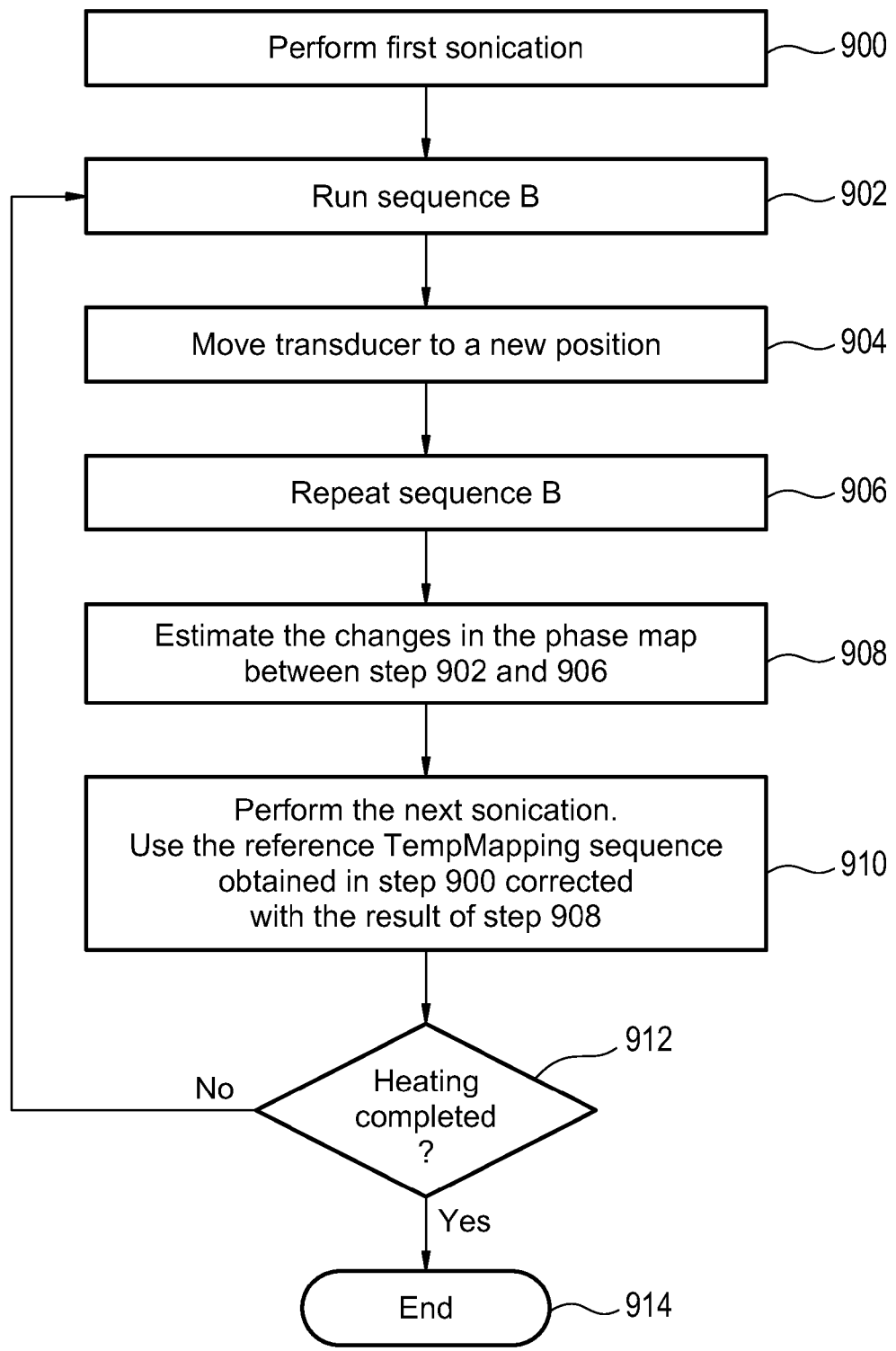
FIG. 9 shows a flowchart which illustrates a method according to a further embodiment of the invention.

FIG. 9 shows a flow diagram which illustrates a method according to a further embodiment of the invention. First in step 900 a heating of the target zone or sonication of the target zone is performed. Next magnetic resonance data is acquired in step 902 with a pulse sequence of type B. In this particular embodiment a pulse sequence of type B is a pulse sequence sensitive to the B0. Typically this kind of sequence is gradient echo sequence where the B0 variation can be seen in the phase map. Sequence of type B should produce phase map and covers a large enough region of interest for the whole treatment volume. Next in step 904 the ultrasonic transducer is moved from its original position to a new position. Next in step 906 the magnetic resonance data is again acquired using the pulse sequence of type B. In this embodiment the transducer was moved from place to place and a phase map was measured in both instances. In PRF method the temperature change is seen as a change in phase map. Transducer movement induced errors in phase maps make the estimation of cumulative heating due several successive sonications difficult. In step 908 an estimate in the change of the phase map between steps 902 and 906 is made. Next in step 910 another sonication of the target zone is performed and the transducer movement induced change in the phase of the temperature mapping sequence may be corrected for. This is particularly useful when a phase type method is used to determine the temperature. Next block 912 is a decision box, the question is is the treatment completed. If the answer is no then the method returns back to step 902. Step 902 may be skipped after the first round in which case the method goes directly to step 904. If the originally acquired magnetic resonance data is used as a reference image for the phase then the monitoring of the cumulative temperature may be calculated. Back to the decision box 912 if the heating is complete then the method ends at step 914.

Figure 10:
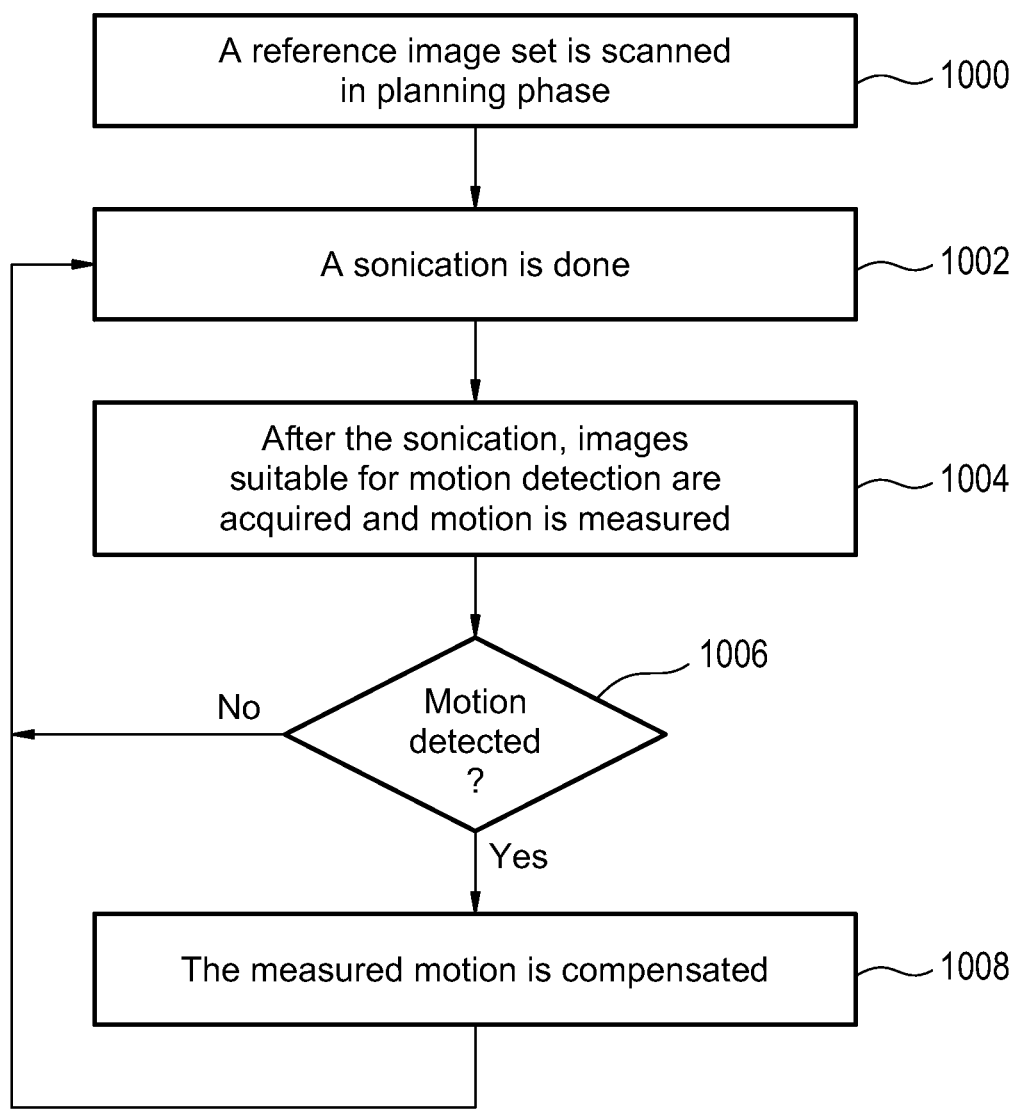
FIG. 10 shows a flowchart which illustrates a method according to a further embodiment of the invention.

FIG. 10 shows a flow diagram illustrating a method according to a further embodiment of the invention. First in step 1000 a reference image is scanned in a planning phase. The reference image can be the image used for planning or an image set specifically acquired for the purpose of later motion detection and/or compensation. Next in step 1002 a sonication or a heating of the target zone is performed. Next in step 1004 images suitable for motion detection are acquired and the motion is measured. This is performed after the sonication. Next box 1006 is a decision box. The question is is motion detected. If no motion is detected then the method loops back again to 1002 and a further sonication or heating is performed. If motion has been detected using the magnetic resonance data or images then the method proceeds to step 1008. In step 1008 the measured motion is compensated for and the treatment plan is corrected. The method then returns back to step 1002.

Means to combat patient movement, cumulative heating effects, and prolonged procedure times are may be beneficial for high-intensity focused ultrasound (HIFU) therapy. The current state of art tries to address these needs by interleaving temperature scan protocols and automated treatment volume positioning.

In one embodiment of the invention subject movement and temperature information scanning is done before and after a sonication. This scanning is henceforward called intermediate scanning. This intermediate scanning may, in some embodiments, correspond to magnetic resonance data acquired with a first pulse sequence, or even various pulse sequences referred to as type A or type B in previous embodiments.

In another embodiment of the invention intermediate scanning is carried out with scan protocol(s) that differ(s) from the protocol used during the sonication.

In another embodiment of the invention, interactive or automated re-planning and result analysis are carried out concurrently with intermediate scanning.

In another embodiment of the invention According to the fourth aspect of the invention, intermediate scanning is triggered automatically by the sonication events, or semi-automatically by user interaction.

In another embodiment of the invention intermediate scanning is used to correct and calibrate the effects of patient movements and ultrasound transducer motion on the temperature mapping images to allow estimation of accumulated temperature.

As mentioned above, the state of the art in HIFU temperature imaging has concentrated on the sonication—the sonication scan protocol or pulse sequence has been optimized for the relatively fast image output, at the expense of morphological data and signal/contrast-to-noise ratio. When tissue has heated up, a cooling period between sonications has been utilized to collect additional data with the suboptimal sonication scan.

Acquisition of other types of image data have resulted in lengthy, manual procedures that are disruptive for the therapy.

Automating the protocol switching can provide image data with arbitrary contrast—using T1-weighed imaging, temperature maps from fatty tissue can be acquired, may result in a more accurate cooling time estimations and prevention of tissue overheating. Extended volumes can be swept or larger 3D volumes imaged to check for temperature buildup outside the normal volume of interest. Patient movement outside sonication can be immediately detected and corrective actions planned.

In the state of art HIFU systems only temperature changes are detected. Absolute measurements of accumulative heath are problematic because of patient movements and effect of transducer motion on the temperature mapping images. Intermediate scanning provides information to correct patient motion and calibrate the effect of transducer motion.

Concurrent planning and analysis can be carried out faster as the user does not need to carry out checks against patient movement or estimate remaining cooling time based on the acquired sonication image data, but to rely on the automated image analysis from intermediate scans.

Embodiments of the invention may provide for a method where pre-sonication or cooling time is utilized to collect image data with altered geometry and image contrast, without the optimizations required for a sonication scan.

When the patient has been placed inside the scanner and is ready for sonications, pre-sonication scanning starts, triggered by the user interface: HIFU software sends a request to the scanner software to switch the currently executing protocol (if any) to the morphologically accurate scan, followed by another request for accurate temperature mapping scan. These form good-quality baselines for subsequent patient movement and temperature change checks, respectively.

When the user triggers a sonication, the executing protocol is automatically switched to the sonication-optimized scan and the sonication is carried out with the said scan.

When the sonication hardware stops, another automated protocol switch takes place to monitor patient movement and temperature development in fatty tissues. Alternatively, sonication-optimized scan may continue some time after the sonication before another protocol or pulse sequence starts. The latter monitoring functionality updates the remaining cooling time automatically, leaving the user to carry out concurrent alterations to the remaining treatment plan.

In some embodiments it is identified that the scan protocol used for monitoring of the temperature rise during sonication can be switched to a different scan protocol. As an alternative to using the magnetic resonance data for measuring temperature, there may however be a multitude of different scan protocols or pulse sequences that are useful to scan between sonications for high-intensity focused ultrasound therapy. For example, several different MR contrasts/parameters can be used to assess tissue therapy response during cool-down and may as such aid in providing a therapeutic endpoint for the session that is not dependent on the temperature imaging. Also, the flow may be estimated with for example non-contrast agent MRA to assess occlusion of tumor feeding vessels. Absolute temperature imaging may also be done via spectroscopy to calibrate the thermometry scan.

Commonly the scan protocol used for monitoring temperature rise during HIFU sonication is a compromise between spatial and temporal resolution as well as spatial coverage and SNR/temperature accuracy. The reason for the fairly high requirement on temporal resolution is the typically high powers used and rapid temperature rise that results. The monitoring scan should be able to detect excessive temperature rise sufficiently fast to avoid damaging healthy structures. Once sonication ends and the cooling period required to allow healthy tissues to cool back down begins, there is no need for rapid temperature estimation. This time period may be utilized for scanning other scan protocols to augment and/or calibrate the temperature information obtained during sonication.

Problems or Disadvantages Overcome by the Invention

For example, the scan can be a conventional thermometry scan (PRF/T1/etc.) or it may be an absolute temperature scan for calibrating the temperature measurement. It may also be an entirely different scan altogether. The cooling period for high intensity focused ultrasound is typically on the order of 1-5 minutes and may thus be utilized for scanning of alternative scan protocols while the therapy plan For example, several MR contrasts and parameters may be used to assess tissue damage. T2w scans may be performed to give an idea of oedema in soft tissues, elastography may give an idea of protein denaturation and resulting stiffening of the tissue, and diffusion imaging may give an idea of alteration of water flow on a cellular level that has also been found to be affected by thermal coagulation.

Moreover, occlusion of vessels may be estimated with non-contrast or contrast enhanced MRA. For some tumors, HIFU induced partial or full embolization may be the goal of the treatment or alternatively a means to provide a more efficient heating for successive sonications. This may be of benefit for iteratively attempting to ablate the tumor feeding vessels as has been seen beneficial in some uterine fibroids, and may also prove beneficial in highly perfused organs such as the liver.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 300 medical apparatus
302 magnetic resonance imaging system
304 magnet
306 bore of magnet
308 imaging zone
310 magnetic field gradient coil
312 magnetic field gradient coil power supply
314 radio frequency coil
316 radio frequency transceiver
318 subject
319 subject support
320 heating system
321 target zone
322 computer system
324 hardware interface
326 processor
328 user interface
330 computer storage
332 computer memory
340 treatment plan
342 first pulse sequence
344 magnetic resonance data
346 heating system commands
350 control module
352 treatment plan modification module
440 second pulse sequence
442 control magnetic resonance data
450 heating system command modification module
500 medical apparatus
502 high intensity focused ultrasound system
504 fluid filled chamber
506 ultrasound transducer
508 mechanism
510 mechanical actuator/power supply
512 path of ultrasound
514 ultrasound window
516 gel pad
518 sonication point
600 medical apparatus
601 radio-frequency heating system
602 antenna
604 radio-frequency transmitter

The invention claimed is:

1. A medical apparatus comprising:
a magnetic resonance imaging system comprising a magnet with an imaging zone configured to acquire magnetic resonance data from a subject from within the imaging zone;
a heating system operable configured to heat a target zone within the imaging zone;
a memory configured to store machine executable instructions;
a processor configured to control the medical apparatus, wherein execution of the instructions causes the processor to receive a treatment plan, and execution of the instructions cause the processor to repeatedly:
control the heating system in accordance with the treatment plan to heat the target zone during alternating heating periods and cooling periods;
acquire magnetic resonance data by controlling the magnetic resonance imaging system, wherein the instructions cause the processor to: acquire the magnetic resonance data from a first region of interest during a cooling period using a first scan protocol selected from at least one of the cooling periods; and acquire control magnetic resonance data from a second region of interest during a heating period using a second scan protocol; and
modify the treatment plan in accordance with the magnetic resonance data, wherein the first scan protocol is different than the second scan protocol.

2. The medical apparatus of claim 1, wherein execution of the instructions further causes the processor to repeatedly acquire the control magnetic resonance data by controlling the magnetic resonance imaging system in accordance with a second pulse sequence, wherein the heating period is chosen from at least one of the heating periods, and wherein the heating system is controlled in accordance with the treatment plan and the control magnetic resonance data.

3. The medical apparatus of claim 2, wherein the control magnetic resonance data comprises first thermal magnetic resonance data, wherein the magnetic resonance data comprises second thermal magnetic resonance data, wherein execution of the instructions causes the processor to calibrate the first thermal magnetic resonance data using the second thermal magnetic resonance data.

4. The medical apparatus of claim 3, wherein the second pulse sequence is a proton resonant frequency pulse sequence, wherein the first pulse sequence is a B0 mapping pulse sequence, wherein the magnetic resonance data is acquired at least two times, the heating system comprises a high intensity focused ultrasound system with a movable transducer, wherein execution of the instructions further causes the processor to:
move the transducer between a first position and a second position after the magnetic resonance data has been acquired once; and
calculate a phase map using the magnetic resonance data.

5. The medical apparatus of claim 2, wherein the control magnetic resonance data comprises first thermal magnetic resonance data, wherein the magnetic resonance data comprises second magnetic resonance thermometry data, wherein the first thermal magnetic resonance data has a first temporal resolution, wherein the second thermal magnetic resonance data has a second temporal resolution, wherein the first temporal resolution is higher than the second temporal resolution.

6. The medical apparatus of claim 2, wherein the second region of interest is smaller than the first region of interest.

7. The medical apparatus of claim 2, wherein the first pulse sequence is operable for controlling the magnetic resonance imaging system such that the magnetic resonance data has less geometric distortion than the control magnetic resonance data.

8. The medical apparatus of claim 2, wherein the first pulse sequence comprises a fat temperature measuring pulse sequence, wherein the magnetic resonance data is acquired at least two times, wherein execution of the instructions further causes the processor to calculate a near field fat temperature map using the magnetic resonance data.

9. The medical apparatus of claim 2, wherein the first region of interest and the second region of interest have an identical area.

10. The medical apparatus of claim 2, wherein the first region of interest and the second region of interest have an identical area and the first region of interest is shifted with respect the second region of interest.

11. The medical apparatus of claim 2, wherein the first region of interest has a first area, the second region of interest has a second area, and the first area is greater than the second area.

12. The medical apparatus of claim 1, wherein the magnetic resonance data is acquired at least two times, wherein execution of the instructions further causes the processor to:
reconstruct a first image and a second image from the magnetic resonance data acquired at the at least two times;
determine a motion map using the first image and the second image; and
modify the treatment plan in accordance with the motion map.

13. The medical apparatus of claim 1, wherein the execution of the instructions further causes the processor to generate an estimated tissue damage map using the magnetic resonance imaging system by analyzing the magnetic resonance imaging data using any one of the following analysis methods: T2w imaging, constructing an elasto graphic map, calculating a diffusion map, determining a diffusion image, determining a non-contrast magnetic resonance angiogram, determining a perfusion map, determining an intra voxel incoherent motion map, calculating a T1 map, calculating a T1rho map, calculating a T2star map, calculating a nuclear magnetic resonance spectrum, and calculating oxygenation level by calculating an oxygen nuclear magnetic resonance spectrum; and wherein the treatment plan is modified in accordance with the tissue damage map.

14. The medical apparatus of claim 1, wherein the magnetic resonance data comprises magnetic resonance angiography data, wherein execution of the instructions further causes the processor to determine a vessel occlusion map using the magnetic resonance angiography data, wherein the treatment plan is modified in accordance with the tissue damage map.

15. The medical apparatus of claim 1, wherein the heating system is any one of the following: high intensity focused ultrasound, radio-frequency heating system, a microwave ablation system, a hyperthermia therapy system, a laser ablation system, and an infrared ablation system.

16. A computer program product comprising machine executable instructions for execution by a processor controlling a medical apparatus, wherein the medical apparatus comprises a magnetic resonance imaging system comprising a magnet with an imaging zone, wherein the magnetic resonance imaging system is operable for acquiring magnetic resonance data from a subject from within the imaging zone, wherein the medical apparatus further comprises a heating system operable for heating a target zone within the imaging zone, wherein execution of the machine executable instructions causes the processor to receive a treatment plan, wherein execution of the machine executable instructions further cause the processor to repeatedly:
- control the heating system in accordance with the treatment plan to heat the target zone during alternating heating periods and cooling periods;
- acquire magnetic resonance data by controlling the magnetic resonance imaging system, wherein the instructions cause the processor to: acquire the magnetic resonance data from a first region of interest during a cooling period using a first scan protocol selected from at least one of the cooling periods; and acquire control magnetic resonance data from a second region of interest during a heating period using a second scan protocol; and
- modify the treatment plan in accordance with the magnetic resonance data, wherein the first scan protocol is different than the second scan protocol.

17. A method of controlling a medical apparatus, wherein the medical apparatus comprises a magnetic resonance imaging system comprising a magnet with an imaging zone, wherein the magnetic resonance imaging system is operable for acquiring magnetic resonance data from a subject from within the imaging zone, wherein the medical apparatus further comprises a heating system operable for heating a target zone within the imaging zone, wherein the method comprises:
- receiving a treatment plan and, after the receiving, repeatedly:
  - controlling the heating system in accordance with the treatment plan to heat the target zone during alternating heating periods and cooling periods;
  - acquiring magnetic resonance data by controlling the magnetic resonance imaging system, wherein the magnetic resonance data from a first region of interest during a cooling period using a first scan protocol; and acquire control magnetic resonance data from a second region of interest during a heating period using a second scan protocol;
  - acquiring control magnetic resonance data from a second region of interest during a heating period; and
  - modifying the treatment plan in accordance with the magnetic resonance data, wherein the first scan protocol is different than the second scan protocol.

18. The computer program product of claim 17, wherein execution of the instructions further cause the processor to repeatedly acquire control magnetic resonance data by controlling the magnetic resonance imaging system in accordance with a second pulse sequence, wherein the instructions cause the processor to acquire the control magnetic resonance data during a heating period chosen from at least one of the heating periods, and wherein the heating system is controlled in accordance with the treatment plan and the control magnetic resonance data.

19. The computer program product of claim 18, wherein:
the first region of interest and the second region of interest have an identical area;
the first region of interest and the second region of interest have an identical area and the first region of interest is shifted with respect the second region of interest; or
the first region of interest has a first area, the second region of interest has a second area, and the first is greater than the second area.

* * * * *